United States Patent [19]

Lapluye et al.

[11] Patent Number: 5,466,608
[45] Date of Patent: Nov. 14, 1995

[54] PROCESS AND APPARATUS FOR HETEROGENEOUS PHASE SYNTHESIS OF MACROMOLECULES SUCH AS PEPTIDES, POLYNUCLOETIDES OR OLIGOSACCHARIDES

[75] Inventors: Gerard Lapluye, Versailles; Roger Poisson, Les-Clayes-sous-Bois, both of France

[73] Assignee: Rhôn-Poulenc Rorer S.A., Anthony, France

[21] Appl. No.: 117,003

[22] PCT Filed: Mar. 4, 1992

[86] PCT No.: PCT/FR92/00197

§ 371 Date: Sep. 7, 1993

§ 102(e) Date: Nov. 8, 1993

[87] PCT Pub. No.: WO92/15867

PCT Pub. Date: Sep. 17, 1992

[30] Foreign Application Priority Data

Mar. 6, 1991 [FR] France .................. 91 02645

[51] Int. Cl.$^6$ .................................................. G01N 33/68
[52] U.S. Cl. .................. 436/86; 436/89; 436/94; 435/6; 435/286.1; 435/286.5; 435/286.7; 422/108; 422/110
[58] Field of Search .............. 436/89, 94; 435/6, 435/287; 422/68.1, 81, 108, 110, 119; 935/86, 87, 88

[56] References Cited

U.S. PATENT DOCUMENTS

| 4,598,049 | 7/1986 | Zelinka et al. | 435/287 |
| 4,603,114 | 7/1986 | Hoal et al. | 436/89 |
| 5,061,635 | 10/1991 | Shively | 436/89 |
| 5,137,695 | 8/1992 | Rusnak et al. | 422/116 |

OTHER PUBLICATIONS

Hawke et al. "Microsequence Analysis of Peptides and Proteins" Anal. Biochem. 147, 315–330 (1985).

*Primary Examiner*—David A. Redding
*Attorney, Agent, or Firm*—Synnestvedt & Lechner

[57] ABSTRACT

Method and device for the synthesis of macromolecules, including peptides, polynucleotides or oligosaccharides. The method and device involves a reactor which contains a solid support on which a component of the product to be synthesized is fixed. The reactor comprises filters at its ends and is mounted movably for rectilinear reciprocating movement in a vessel which contains a reactive liquid. A temperature probe is provided to detect the temperature variations of the reactive liquid due to passage into and out of the reactor. The progress of coupling and deprotection reactions which occur in the synthesis of peptides, polynucleotides and oligosaccharides is monitored.

22 Claims, 2 Drawing Sheets

PROCESS AND APPARATUS FOR HETEROGENEOUS PHASE SYNTHESIS OF MACROMOLECULES SUCH AS PEPTIDES, POLYNUCLOETIDES OR OLIGOSACCHARIDES

FIELD OF THE INVENTION

The invention relates to a process and an apparatus for heterogeneous phase synthesis of molecules and macromolecules such as peptides, oligo- or polynucleotides or oligo- or polysaccharides.

BACKGROUND OF THE INVENTION

Synthesis of these molecules on a solid support, in particular the synthesis of peptides, is well known from the work of MERRIFIELD in 1963 and is widely used. It essentially comprises sequentially assembling amino acids to form a peptide, by fixing one end of the chain to an insoluble support such as a polymer. Once the desired sequence of amino acids has been sequentially assembled, this chain is cleaved to separate the peptide from the support and release it in solution.

The reactions brought into play in this synthesis are essentially reactions of coupling of amino acids, performed alternately with reactions of stripping desired functions of the amino acids, and washing and rinsing operations between the end of one reaction and the beginning of the next reaction.

It is essential in this synthesis that each coupling or stripping reaction be performed to 100%, or almost. The only means that currently makes it possible to ensure this is to interrupt the synthesis to carry out a test or an assay. This considerably prolongs the length of a synthesis and prevents it from being automated. Moreover, the tests used do not always permit verification of whether a reaction has taken place completely, so that in the event of uncertainty the reaction must be restarted for increased certainty.

Finally, in these classic synthesis processes it is generally necessary to use excess ingredients and coupling reagents, for many reasons (inaccessibility of some of the reaction sites of the polymer, weak attachment of the ingredients on the polymer or on an ingredient already fixed to the polymer, and so forth).

All these disadvantages mean that classic peptide synthesis processes have a low yield, of the order of 20 to 30%, as a function of the length of the peptide chain, and that the cost of peptides is extremely high (sometimes more then 1000 FF/milligram of peptide).

In an attempt to reduce these disadvantages, the proposal has already been made to monitor the coupling reactions with ultraviolet spectroscopy, which is believed to detect a peak signal corresponding to the end of the coupling reaction. However, the results have shown that this method was not very reliable and could lead to errors or major difficulties in interpretation.

It has also been proposed that the electrical conductance of the reaction medium be measured. However, this medium is particularly heterogeneous, and in this process considerable background noise in which the useful signal is embedded is detected, which makes the process difficult to exploit.

The object of the invention is essentially to provide a simple, effective and particularly reliable solution to the problem of monitoring coupling and stripping reactions performed in peptide, polynucleotide or oligosaccharide syntheses.

It is based on the fact that each coupling or stripping reaction causes a variation in temperature of the reaction medium, and that under certain conditions it may be assumed that the reaction is completed once this variation in temperature becomes substantially zero.

However, it is virtually impossible directly to measure this variation in temperature, because it is much slighter (by one or more orders of magnitude) than the variations in temperature due to parasitic reactions in the reaction medium, notably reactions between solvents.

One of the essential merits of the present invention is accordingly that of successfully detecting the very slight variation in temperature of the reaction medium that accompanies a coupling or stripping reaction, and of monitoring the development of this variation in temperature very precisely in order to detect the end of the coupling or stripping reaction surely and reliably.

SUMMARY OF THE INVENTION

Accordingly, the invention proposes a process for heterogeneous phase synthesis of macromolecules such as peptides, polynucleotides or oligosaccharides, consisting in arranging a solid support, such as a polymer, in a tubular reactor, in sequentially dosing and introducing reagent liquids into the reactor, in order successively to effect the desired reactions, in particular coupling and stripping reactions, alternating with operations of washing and rinsing the reactor and the solid support, the process being characterised in that it consists in closing the upper and lower ends of the reactor with filters that retain the solid support and allow liquids to pass, then, for each reaction to be performed, in causing the corresponding reagent liquid to circulate repeatedly and alternately in the reactor and through the aforementioned filters, and in monitoring the development of the ongoing reaction by detecting the variations in temperature of the reagent liquid associated with its passages in the reactor and outside the reactor, the end of the reaction corresponding to a substantially zero value of these variations in temperature after a progressive decrease over a predetermined period of time.

The repeated and alternating circulation of the reagent liquid in the reactor makes it possible to perform a kind of modulation of the variation in temperature of this reagent liquid, which is due directly to an ongoing coupling or stripping reaction, and hence to demonstrate this slight variation in temperature with respect to a global, much greater variation in the temperature of the reagent liquid due to the parasitic reactions of esterification of amino acids, interaction between groups, and essentially reactions with mixtures of solvents.

Preferably, the circulation of the reagent liquid in the reactor and outside of it is periodic and vertical.

In choosing the appropriate frequency of this alternating periodic circulation, the modulation of the variation in temperature due to a coupling or stripping reaction can easily be demonstrated, the frequency of this modulation corresponding to that of the alternating periodic circulation of the liquid.

In a preferred embodiment of the invention, the process consists in displacing the reactor in an alternating vertical rectilinear motion in a vessel containing the reaction liquid.

According to yet another characteristic of the invention, the process consists in continuously detecting the temperature of the reagent liquid at a point located in the immediate vicinity of a filter of the reactor, the point for detection of the temperature being linked to the reactor in order to monitor the latter in its alternating motion, and being advantageously located outside the reactor, in a passage for guiding the reagent liquid to the corresponding end of the reactor.

The sensitivity of detection of the variations in temperature of the reagent liquid is thus improved.

The invention also proposes an apparatus for heterogeneous phase synthesis of macromolecules such as peptides, polynucleotides or oligosaccharides, this apparatus comprising a tubular reactor containing a solid support such as a polymer, and means for sequential dosage, supply and evacuation of reagent liquids and liquids for washing and rinsing the reactor and the solid support, characterised in that the tubular reactor is closed at its ends with filters that retain the solid support and allow liquids to pass, and in that the apparatus comprises means for causing the reagent liquid to circulate repeatedly and alternately in the reactor and through the aforementioned filters, and means for detecting variations in temperature of the reagent liquid associated with its passages in and outside the reactor.

Preferably, the reactor is mounted movably for alternating vertical rectilinear motion in a vessel comprising means for supply and evacuation of the aforementioned liquids, and is connected to motor means for displacement.

The reactor is mounted to slide in a sealed manner in this vessel, and includes at its ends sealing gaskets, cooperating with a cylindrical wall of the vessel and between them trapping a layer of gas, for example air, forming a thermal insulation of the reactor.

The aforementioned temperature detection means comprise at least one temperature probe, such as a thermistor, placed in contact with the reagent liquid at a point located in the vicinity of one of the end filters of the reactor.

This temperature probe is advantageously connected to an input of an information processing system, the outputs of which are connected to means for controlling dosage, supply and evacuation of the aforementioned liquids, and optionally to motor means for displacement of the reactor in said vessel.

Means for recording and/or displaying the output signal of the temperature probe may also be provided.

BRIEF DESCRIPTION OF THE DRAWINGS

The invention will be better understood and further characteristics, details and advantages thereof will become more apparent from reading the ensuing description given by way of example, with reference to the accompanying drawings, in which.

DETAILED DESCRIPTION OF THE INVENTION

Figure 1:
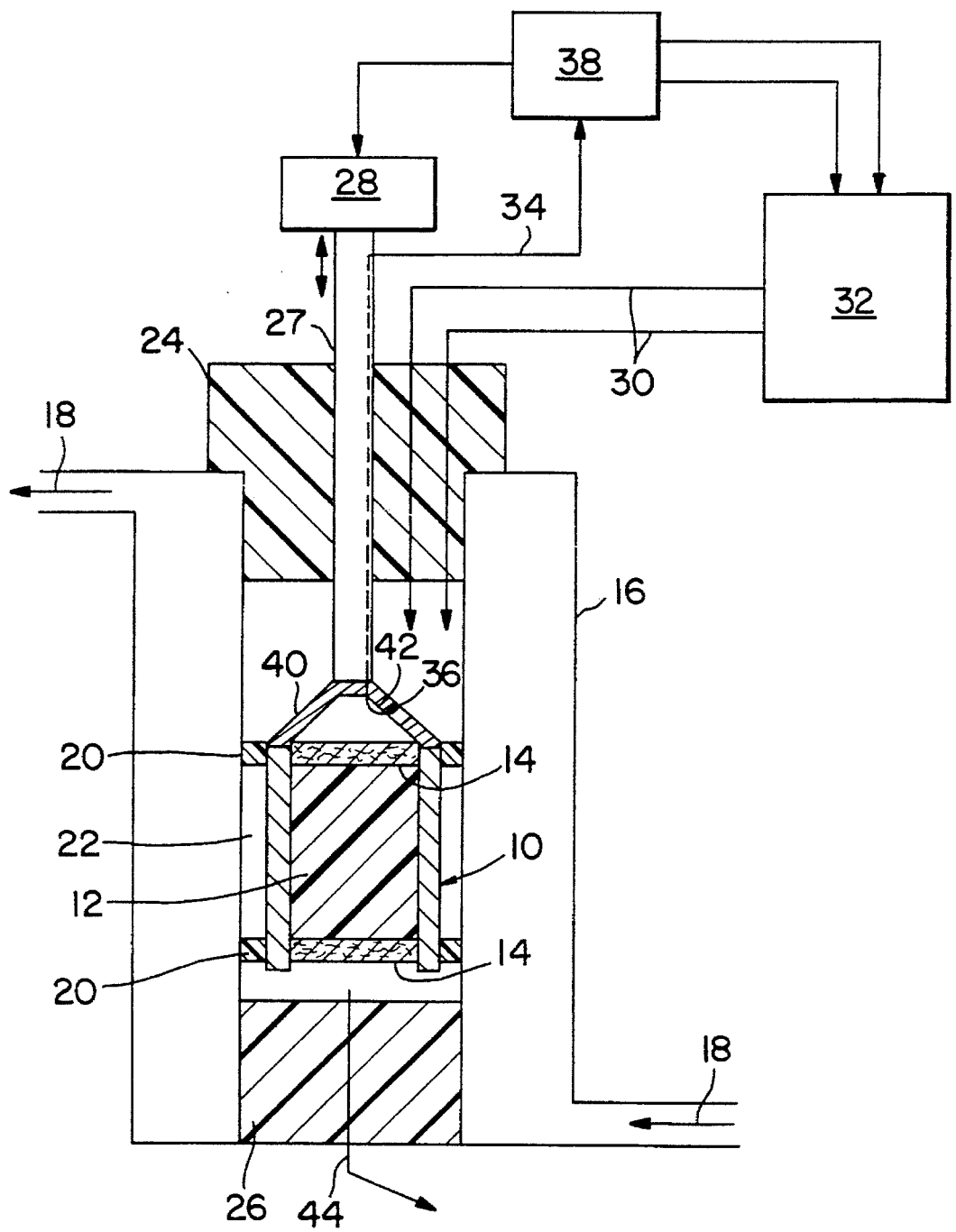
FIG. 1 schematically shows an apparatus according to the invention.

In FIG. 1, an apparatus according to the invention is schematically shown, and is usable in particular for the synthesis of peptides, polynucleotides or oligosaccharides.

This apparatus essentially comprises a tubular reactor 10, for example cylindrical in shape, intended to contain a solid support 12, such as a resin, for example, and the axial ends of which are closed with filters 14 permitting retention of this resin while allowing the reagent liquids and the washing and rinsing liquids to pass.

Typically, the filters 14 consist of discs of porous or microporous material that is insensitive to the solvents and agents involved in the reactions to be performed. For example, microporous discs of sintered glass, metal, polytetrafluoroethylene, fluorinated elastomer, and so forth, may be used.

In the embodiment shown, the reactor 10 is mounted to slide vertically in a sealed manner in a cylindrical double-walled vessel 16 which is kept at constant temperature, for example by circulation of a thermoregulated liquid, in the direction indicated by the arrows 18.

At its ends, the reactor 10 includes sealing gaskets 20, for example of polytetrafluoroethylene, which cooperate with the inside cylindrical wall of the vessel 16 and between them trap an annular layer 22 of gas, for example air, which forms a thermal insulation of the reservoir 10.

The upper and lower ends of the vessel 16 are closed with stoppers 24 and 26, respectively, for example of polytetrafluoroethylene, which include means for supplying and evacuating the reagent liquids and the washing and rinsing liquids.

More precisely, the upper stopper 24 of the vessel 16 is pierced on the one hand by a rectilinear rod 27 that connects the reactor 10 to motor means 28 for displacing the reactor in alternating rectilinear motion in the vessel 16, and on the other hand, by tubes 30 for supplying the aforementioned liquids, which are connected upstream to automatic means 32 for dosage and distribution.

The aforementioned rod 27 may be tubular, so as to receive the leads 34 connecting a temperature probe 36 to an input of an information processing system 38, which comprises means for recording and/or displaying a temperature signal.

The temperature probe 36, such as a thermocouple, a thermistor, or any other suitable means, is located in the immediate vicinity of a filter 14 of the reactor 10, outside this reactor and inside a liquid passage, this passage being formed for example by a frustoconical lid 40 that caps the upper end of the reactor 10 and includes an opening 42 in which the temperature probe 36 is accommodated.

The information processing system 38 is advantageously programmed to control the motor means 28 and the means 32 for dosing and distributing the liquids.

The lower stopper 26 of the vessel 16 in turn includes a conduit 44 for evacuating the liquids.

The apparatus according to the invention is for example used in the following way:

First, a quantity of support polymer (for example microbeads of resin), is placed into the reactor, the quantity being determined as a function of the volume of this reactor and the quantity of peptide, polynucleotide or oligosaccharide to be synthesised.

The reactor 10, provided with its filters 14, is then placed inside the vessel 16, by being connected to the drive means 28.

A first step of the process consists in neutralising the support polymer, by rinsing with DIEA (diisopropylethylamine), diluted in DCM (dichloromethane), and then by rinsing with DCM.

The reagent powders [HOBT (1-hydroxybenzotriazole), BOP (benzotriazoly-N-oxy-tris-(dimethylamino)phosphonium hexafluorophosphate), t-BOC-A.A. (tert-butyloxycarbonylamino acid)] are waiting in a container. A mixture of DCM and DMF (dimethylformamide) is taken up and introduced into the container that contains the powders. These are dissolved, and then the liquid mixture is next introduced into the reactor 10.

Simultaneously, a quantity of DIEA is added to the mixture in the reactor, and the reactor is displaced in alternating rectilinear vertical motion in the vessel 16 by the motor means 28. This alternating motion is continuous, its frequency being two back-and-forth motions per minute, for example, for a coupling reaction, and from seven to ten back-and-forth motions per minute for a rinsing. The course of displacement of the reactor 10 in one or the other direction is determined preferably in such a way that the volume of liquid penetrating into the reactor by one end and emerging from the reactor by the other end is substantially equal to the volume left free in the reactor by the support polymer.

This alternating rectilinear motion of the reactor in the vessel 16 results not only in an alternating periodic circulation of the reagent liquid inside the reactor but also in agitation and placement in suspension of the support polymer inside the reactor. For example, if the support polymer is denser than the reagent liquid, the upward motion of the reactor results in a kind of settling of the support polymer to the bottom of the reactor, while its downward motion results in a resuspension of the support polymer in the reactor. Moreover, the alternating motion of the reactor has the effect of cleaning the pores of the filters 14, which would otherwise be likely to become progressively plugged up with the support polymer.

The probe 36 makes it possible to monitor the development of the ongoing reaction (a reaction of coupling or a reaction of stripping of a function of an ingredient).

Figure 2:
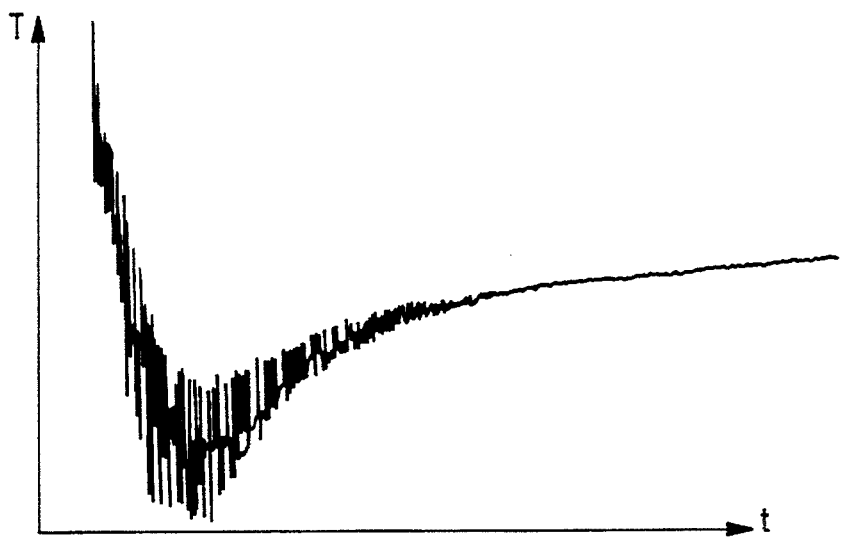
FIGS. 2, 3 and 4 schematically show the variations in temperature of a reagent liquid that are due to coupling and stripping reactions, respectively.

In FIG. 2, the curve of the variation in the output signal of the probe 36 is shown as a function of time, in the course of a coupling reaction, which in this specific case was an Asn-Gly (asparagine-glycine) coupling reaction. It is seen that this curve includes a sawtooth oscillation about a mean value that decreases quite rapidly and then increases again up to a substantially constant value, and that the amplitude of the sawtooth oscillation decreases progressively in the course of time and then becomes substantially zero.

This curve can be interpreted as follows:

The sawteeth represent the variations in temperature of the reagent liquid that are due to the back-and-forth motions of the reactor 10 in the vessel 16. When the reactor descends in the vessel from its top dead centre point, the liquid present in the reactor passes through the upper filter 14, fills the frustoconical lid 40 and emerges via its orifice 42 and arrives in the upper portion of the vessel. The signal furnished by the probe 36 then corresponds to the temperature of the liquid that has undergone the coupling reaction. Conversely, when the reactor 10 rises in the vessel 16 from its bottom dead centre point, the liquid contained in the reactor 10 emerges from it, passing through its lower filter 14, and the liquid contained in the upper portion of the vessel 10 [sic] above the reactor penetrates into the frustoconical lid 40, passing through the orifice 42, and then re-enters the reactor 10, passing through the upper filter 14.

The temperature probe 36 is thus successively present in the reagent liquid that has just undergone a coupling reaction, and then the reagent liquid that is about to participate again in the coupling reaction.

When the output signal of the probe 36 no longer exhibits any sawtooth oscillation corresponding to the motion of the reactor, this signifies that the coupling reaction is completed.

Experience has made it possible to verify, by tests and assays, that this has been true for all the coupling reactions and all the stripping reactions used.

Figure 3:
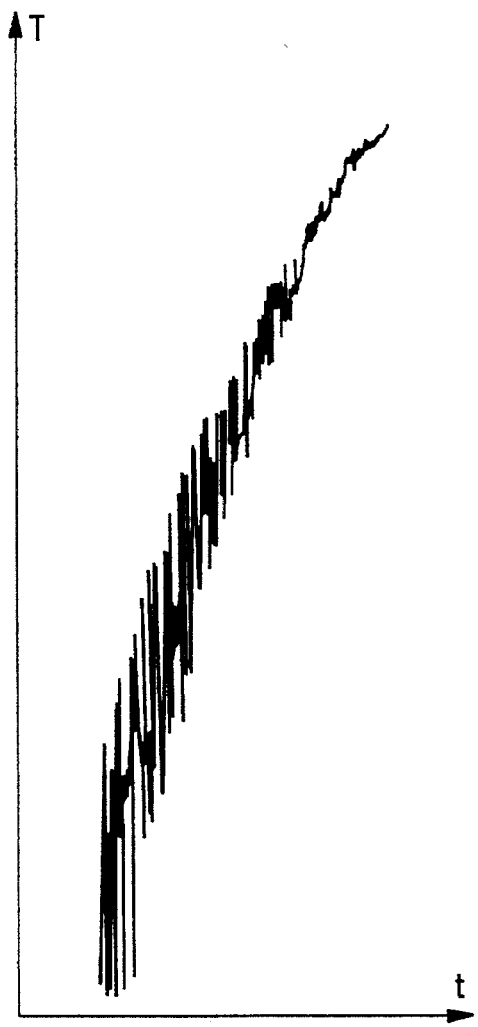

FIG. 3 shows the variations in the output signal of the probe 36 during a stripping reaction (release of an $\alpha$-$NH_2$ function to TFA (trifluoroacetic acid)).

Figure 4:
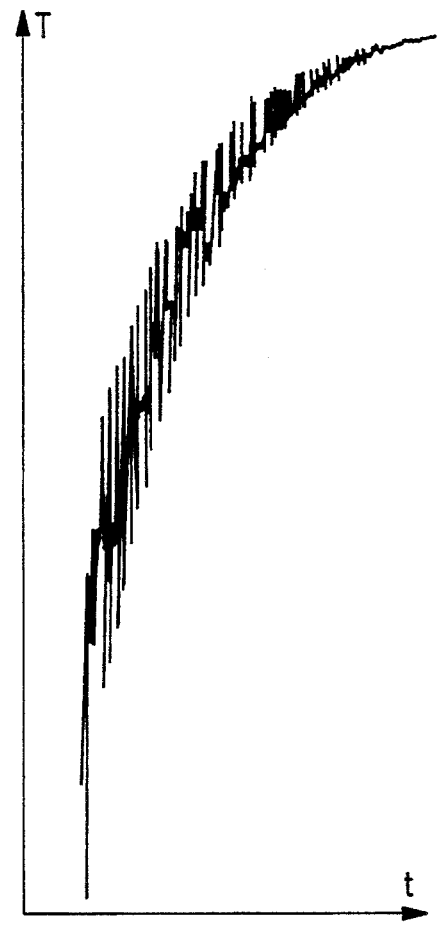

FIG. 4 shows the variations in this output signal during a Gly-resin coupling.

From the curves in FIGS. 2, 3 and 4, it is seen that the mean value of the output signal of the temperature detection probe can vary quite markedly with respect to the amplitude of the sawtooth oscillation, this variation in the mean value being due essentially to secondary esterification reactions, interactions between groups of ingredients, and above all to the emission of heat brought about by the mixtures of solvents. The amplitudes of the sawtooth oscillation may be of the order of $\frac{1}{10}$ of a degree C., while the mean value of the probe output signal may vary by several degrees C in the course of one reaction. Nevertheless it is unnecessary to know either the mean value of the thermal probe output signal or the amplitude of its sawtooth oscillation. To verify that a coupling or stripping reaction is proceeding normally and being completed, it suffices to confirm that the amplitude of the sawtooth oscillation of the thermal probe signal is decreasing progressively, finally fading to nothing at the end of a period of time, the order of magnitude of which is known (generally from 10 to 30 minutes, depending on the type of reaction).

Hence this output signal of the thermal probe can be analysed without difficulty by an information processing system of a conventional type, which at the end of the reaction can control the passage to the next phase of the process or, if a reaction is not proceeding correctly, it can detect and signal anomalous function (for example, blockage of a valve, improper function of a dispenser, etc.).

Accordingly the invention makes it possible automatically to monitor the progress of the coupling and stripping reactions and, without sampling or interrupting the process, to verify that a reaction has proceeded correctly and is completed, before passing to the next phase of the process.

Generally, the invention makes it possible to synthesise peptides with a yield greater than 95% after cleavage, before any purification, while using approximately half as much amino acid per support equivalent as in the prior art.

For example, a decapeptide, ACP 63–74 (corresponding to the amino acids 63 to 74 of the acyl carrier protein) has been synthesised in 15 hours of apparatus function, spread over two days. The temperature of the vessel was regulated at 25° C. It was possible to obtain, after cleavage, 350 mg of peptide for 1 g of starting peptidyl resin, 96% of the mass of this peptide being composed of the decapeptide sought.

Similarly, a tetrapeptide Val-Tyr-Gly-Gly was synthesised with a degree of purity of 97.3% after cleavage, and a tripeptide Gly-Val-Ala was synthesised with a degree of purity of 98.5% after cleavage.

The invention is equally applicable to the syntheses of polynucleotides and oligosaccharides, and in the same manner as described above makes it possible to monitor the reactions employed in these syntheses.

Moreover, numerous modifications may be made to the embodiment that has just been described, without departing from the scope of the invention. For example, two temperature probes may be used, one placed inside and the other outside the reactor, and the variation in the difference between their output signals can be monitored.

Instead of displacing the reactor in an alternating rectilinear motion in a vessel, it is also possible to leave it fixed, and to cause the reagent liquid to circulate in an alternating manner in the reactor.

We claim:

1. A process for the heterogeneous phase synthesis of macromolecules, including peptides, polynucleotides or oligosaccharides, comprising:
   (A) providing a tubular reactor having an upper end and a lower end and a solid support, the upper and lower ends of the reactor comprising filters which retain the solid support and which allow liquids to pass therethrough;
   (B) sequentially dosing and introducing reagent liquids into the reactor successively to effect coupling and stripping reactions;
   (C) causing the reagent liquid to circulate repeatedly and alternately in the reactor and through the filters for each reaction to be performed;
   (D) monitoring the development of the ongoing reaction by detecting the variations in temperature of the reagent liquid associated with its passages in the reactor and outside the reactor, the end of the reaction corresponding to a substantially zero value of these variations in temperature after a progressive decrease over a predetermined period of time; and
   (E) alternating the coupling and stripping reactions with operations of washing and rinsing the reactor and the solid support.

2. A process according to claim 1, comprising circulating alternately the liquid in the reactor periodically.

3. A process according to claim 2 comprising circulating alternately the liquid in the reactor vertically.

4. A process according to claim 3 comprising displacing the reactor in an alternating, vertical and rectilinear motion in a vessel containing the reagent liquid.

5. A process according to claim 4 comprising continuously detecting the temperature of the reagent liquid at a point located in the immediate vicinity of one of the filters.

6. A process according to claim 5 comprising detecting the temperature of the reagent liquid during the alternating motion of the reactor with a temperature detecting means which is linked to the reactor.

7. A process according to claim 6 wherein the temperature detecting means is located outside the reactor and in a passage which guides the reagent liquid into and out of the reactor.

8. A process according to claim 7 wherein the volume of reagent liquid circulating in the reactor during each displacement thereof is substantially equal to the volume of reagent liquid which is left free in the reactor by the support polymer.

9. A process according to claim 8 wherein the reactor is thermally insulated.

10. A process according to claim 1 wherein the solid support comprises a polymeric solid support.

11. An apparatus for the heterogeneous phase synthesis of macromolecules, including peptides, polynucleotides or oligosaccharides, comprising:
   (A) a vessel for housing a tubular reactor;
   (B) a tubular reactor which contains a solid support and which is closed at its ends with filters that retain the solid support while permitting liquids to pass therethrough, the reactor being slidably mounted in the vessel and including at its ends sealing gaskets which cooperate with a cylindrical wall of the vessel to form a cavity in which a layer of gas is sealably trapped therein such that the reactor slides in a sealed manner and to provide thermal insulation;
   (C) means for sequential dosage, supply and evacuation of reagent liquids and liquids for washing and rinsing the reactor and the solid support;
   (D) means for detecting variations in temperature of the reagent liquid;
   (E) motor means connected to the reactor for displacement thereof in the vessel to cause the reagent liquid to circulate repeatedly, alternately and periodically in the reactor and through the filters, wherein the temperature detecting means detects variations in temperature of the reagent liquid, the variations being associated with the passages of the liquid into and out of the reactor.

12. An apparatus according to claim 11 further comprising means for maintaining the vessel at a constant temperature.

13. An apparatus according to claim 12 further comprising means for maintaining the vessel at a constant temperature by circulation of a thermoregulated liquid.

14. An apparatus according to claim 11 wherein the temperature detection means comprises at least one temperature probe.

15. An apparatus according to claim 14 wherein the temperature probe is attached to the outside of the reactor.

16. An apparatus according to claim 15 wherein the temperature probe is located in a passage that conducts the reagent liquid into and out of the reactor.

17. An apparatus according to claim 16 wherein said temperature probe is connected to an input of an information processing system, the outputs of which are connected to means for controlling dosage, supply and evacuation of the reagent liquids.

18. An apparatus according to claim 17 wherein the function and the succession of the coupling and stripping reactions are controlled by the information processing system.

19. An apparatus according to claim 14 wherein the temperature probe comprises a thermistor.

20. An apparatus according to claim 14 wherein the temperature probe is contacted with the reagent liquid at a location which is proximate one of the filters.

21. An apparatus according to claim 11 wherein the gas which is trapped in the cavity comprises air.

22. An apparatus according to claim 11 wherein the solid support comprises a polymeric solid support.

* * * * *